United States Patent [19]

Kalt

[11] Patent Number: 4,917,112
[45] Date of Patent: Apr. 17, 1990

[54] UNIVERSAL BANDAGE WITH TRANSPARENT DRESSING

[75] Inventor: Glenda G. Kalt, Boca Raton, Fla.

[73] Assignee: Kalt Medical Corp., Boca Raton, Fla.

[21] Appl. No.: 234,876

[22] Filed: Aug. 22, 1988

[51] Int. Cl.⁴ .............................................. H61L 15/00
[52] U.S. Cl. ...................................... 128/156; 128/155; 128/888; 128/890; 128/893; 604/304; 604/306; 604/307
[58] Field of Search ............... 128/155, 156, 335, 847, 128/849, 851, 888; 604/174, 180, 307

[56] References Cited

U.S. PATENT DOCUMENTS

| | | | |
|---|---|---|---|
| 2,221,758 | 11/1940 | Elmquist | 128/888 |
| 2,273,873 | 2/1942 | Klein . | |
| 2,949,443 | 8/1960 | Merriam et al. . | |
| 4,181,127 | 1/1980 | Linsky et al. . | |
| 4,324,237 | 4/1982 | Buttaravoli . | |
| 4,341,207 | 7/1982 | Steer et al. | 128/155 |
| 4,341,208 | 7/1982 | Gordon . | |
| 4,485,809 | 12/1984 | Dellas . | |
| 4,669,458 | 6/1987 | Abraham et al. . | |
| 4,744,355 | 5/1988 | Faasse, Jr. . | |

OTHER PUBLICATIONS

The 3-M Tegaderm Transparent Dressing Brochure by the 3-M Company.
Conmed Venigard Disposable Dressing Disclosure.
Co Med Veni-Gard Bandage Brochure, Catalog Nos. 705-4431 and 730-4432.
ConMed Veni-Gard Bandage Brochure, Catalog Nos. 740-1440 and 745-1441.

Primary Examiner—Richard J. Apley
Assistant Examiner—N. Paul
Attorney, Agent, or Firm—Dickstein, Shapiro & Morin

[57] ABSTRACT

A transparent bandage for substantially sealing a wound consisting of a semi-rigid frame for defining an opening and a resilient transparent membrane member substantially covering the opening in order to form a transparent window. The transparent material is such that air and vapors can permeate the material in a first direction and contaminants and fluids are prevented from entering the wound area from an opposite direction. A flap can be secured to the frame such that a user cannot see any of the wound covered by the transparent material when the flap is closed. Several embodiments of the invention are shown consisting of different shapes for different medical needs. A third and fourth embodiment are included for holding tracheal or other types of tubes to a patient such that the area around which the tube is inserted can be readily observed.

25 Claims, 3 Drawing Sheets

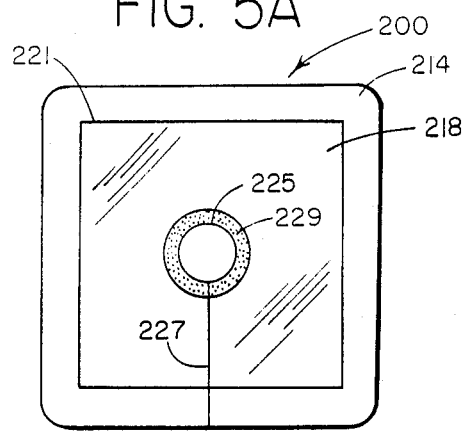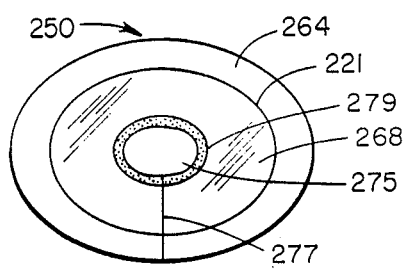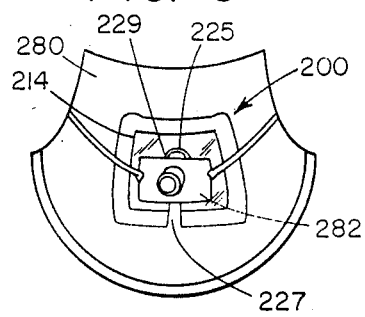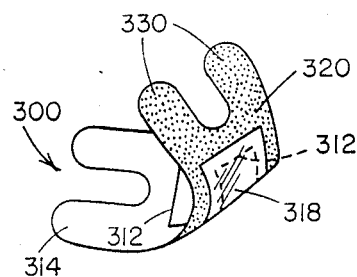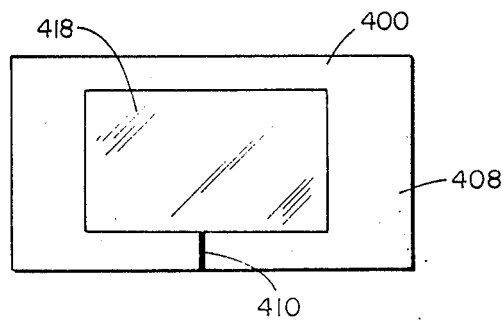

UNIVERSAL BANDAGE WITH TRANSPARENT DRESSING

BACKGROUND OF THE INVENTION

The present invention relates in general to a bandage for covering a particular part of a patient's body such that a desired area can be exposed for view while it is also allowed to heal.

Although the opaque bandage has long been in use, its design suffers from several drawbacks. First, the patient or person treating the patient has no idea how well the wound is healing until the bandage is entirely removed. Second, removal of the bandage increases the danger that the scab or skin covering the wound will be removed along with the bandage. Another drawback is that many bandages fail to adequately aerate the wound. In such instances, the healing of the wound is much slower. Finally, a drawback to many conventional bandages is that part of the wound area is contacted by an adhesive portion of the bandage. Thus, when the bandage is removed, the tacky surface of the bandage will possibly harm the partially healed area.

To date, a number of bandages have been devised which attempt to solve some or all of these drawbacks. However, each of these approaches either involves a complex, difficult to use construction, or fails to provide an adequate solution to some or all of the above problems.

For example, the 3-M Company markets a transparent bandage under the trademarked name "TEGADERM" Transparent Dressing. The bandage consists of a transparent air and vapor permeable film that has the surface of one side entirely coated with an adhesive. The bandage comes supplied with a releasable paper frame adhered to the non-adhesive side of the sheet. The frame is used to maintain the integrity of the bandage's shape before it is applied to the patient's skin, whereupon the frame is removed. Although the "TEGADERM" bandage is relatively simple in its construction, the adhesive surface may harm the healing tissue when the bandage is removed. Moreover, water or contaminants may seep into the wound site from the sides of the bandage.

Another transparent bandage is sold under the registered trademark "VENI-GARD" by the Conmed Corporation. "VENI-GARD" is a disposable dressing for holding an I.V. needle or catheter in a patient's vein. The "VENI-GARD" provides a sterile barrier over the puncture site and incorporates transparent semi-permeable membrane material as the covering over the site. The purpose of the transparent membrane is to allow unobstructed visualization of the puncture locus while at the same time enabling the evaporation of any moisture that collects around the puncture site. However, the construction of the VENI-GARD bandage is complex. Further, the membrane is coated with an adhesive that renders the VENI-GARD unsuitable for use in covering a wound because the adhesive surface may harm the healing tissue when the bandage is removed.

Another example of a transparent bandage is shown in the Gordon patent, U.S. Pat. No. 4,341,208. The Gordon bandage has a transparent window and a flexible frame for adhering the window to the patient's skin. Thus, unlike "VENI-GARD," the Gordon bandage does not contact the adhesive layer to the wound. However, the material used with the window does not allow for the passage of air or moisture from the patient's skin to the exterior surface of the bandage. Moreover, the construction of the Gordon bandage requires a multiple layered window which employs an applicator layer adjacent to the transparent layer. The applicator spaces the window from the skin by the thickness of the frame which is not as sterile as an adjacent film because the spaced film traps air or other substances adjacent to the skin.

Another transparent bandage is illustrated by the Klein patent, U.S. Pat. No. 2,273,873. The Klein bandage involves a transparent adhesive sheet adapted to be used as a dressing for a wound. The wound is not sealed from outside contaminants since air passages are provided along portions of the frame of the bandage. In addition, the transparent material used in Klein bandage is not air or vapor permeable, and the sheet does not contact the skin.

The Linsky et al. patent, U.S. Pat. No. 4,181,127, illustrates a non-adherent wound dressing employing an absorbent pad border that removes moisture from the area around the wound. A transparent film covers the wound and has its edges overlapped by an adhesive frame. However, the film is placed on top of the frame rather than below it, the materials of the frame are primarily webbing, and the film is an imperforate material that does offer the advantages of a transparent air/vapor permeable barrier.

The Merriam et al. patent, U.S. Pat. No. 2,949,443, illustrates a water vapor permeable dressing applied directly to a surgical wound. The material is primarily transparent and water and vapor permeable. However, the material is either applied to the skin through the use of an adhesive layer formed along the outer edge of the dressing, or through the application of an alcohol solvent applied to the skin directly. This construction does not adhere strongly and may easily come loose from the wound area.

The Faasse, Jr. patent, U.S. Pat. No. 4,744,355, discloses a hinged releasable wound dressing in which a thin flexible polymeric film having an adhesive layer coated on one side of the bandage is applied directly to the site of the wound. The Faasse, Jr. bandage has the drawback of directly contacting the wound with adhesive which could cause the healing layer of skin to be pulled up when the bandage is removed.

Finally, the Dellas bandage illustrated in U.S. Pat. No. 4,485,809 provides for a transparent moisture vapor permeable film dressing. As in Faasse, Jr., the Dellas film also employs a skin adhesive in order to directly contact the dressing to the patient's skin. Therefore, the construction of the Dellas dressing can cause tearing of the partially healed wound when the dressing is removed from the patient's skin.

SUMMARY OF THE INVENTION

The present invention alleviates to a great extent the disadvantages presented by the prior devices by providing for a transparent bandage of simple construction that completely seals a wound with a transparent gas/vapor permeable membrane, while avoiding contact between the bandage's adhesive and the wound. The material of the transparent member is air/vapor permeable only in the direction away from the wound such that outside contaminants cannot enter inside the bandage. The frame that adheres the transparent membrane to the wound is semi-rigid yet sufficiently flexible so that the bandage can be comfortably worn while not folding over itself when applied to the skin. In one embodiment, the bandage includes a flap that substantially covers the transparent membrane while allowing air/vapor to pass.

In another embodiment of the invention, the transparent bandage is substantially rectangular. The frame portion consists of a rectangular piece having a centrally defined opening. A similarly shaped but smaller rectangular transparent membrane is attached to the bottom of the frame such that a tacky adhesive border surrounds the membrane portion. A liner is adhered to this tacky border. In use, the liner is peeled away exposing the tacky adhesive surface which is then used to hold the membrane to the patient's skin.

In another aspect of the invention, the bandage is substantially circular.

In still yet another embodiment of the invention, the bandage has a frame with two fingers at opposing ends of the frame. A transparent window is formed in the center of the frame.

It is an object of the invention to provide for a transparent bandage yielding to the foregoing advantages that effectively holds a tube against a patient's body.

It is still a further object of the invention to provide for a transparent tube-holding bandage that is suited for holding a trachea tube to the patient's throat.

It is still an additional object of the invention to provide for a transparent bandage where the bandage does not have to be removed in order for the patient to observe the site of the wound.

It is still a further object of the invention to provide for a bandage of simple construction having a frame consisting of a single piece of material.

It is still a further object of the invention to provide for a bandage yielding to the foregoing advantages and that can clamp to a variety of sizes of tubes and yield to any skin surfaces of the body.

These and other objects of the invention are accomplished by the present invention as described by the drawings and detailed description herein.

BRIEF DESCRIPTION OF THE DRAWINGS

FIGS. 5a-5b are top views of a third embodiment and fourth embodiment of a transparent bandage according to the present invention;

FIG. 6 is a perspective view of the fifth embodiment of FIG. 5a in use;

FIG. 7 is a perspective view of a sixth embodiment of the transparent bandage of the present invention;

FIG. 8 is a top view of a seventh embodiment of the transparent bandage of the present invention; and FIGS. 9a-9b are respectively perspective views of the first embodiment in use and the seventh embodiment in use.

DETAILED DESCRIPTION OF THE PREFERRED EMBODIMENTS

As referred to herein, the inner surfaces of various component parts of the preferred embodiments of the present invention are those surfaces oriented towards the object to which the bandage is adhered. Similarly, the outer surfaces of the various component parts of the preferred embodiments are those surfaces oriented away from such an object. Such an object may be any kind that is used for transparent bandages but will most likely be a patient's skin, their clothing, hair, or the like.

Figure 2:
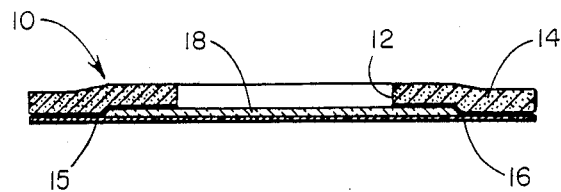
FIG. 2 is a cutaway view taken along section line II—II of FIG. 1.
Figure 1:
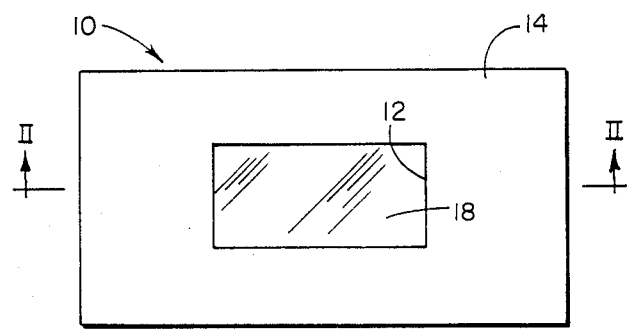
FIG. 1 is a top view of the first embodiment of a transparent bandage according to the present invention.
Figure 3:
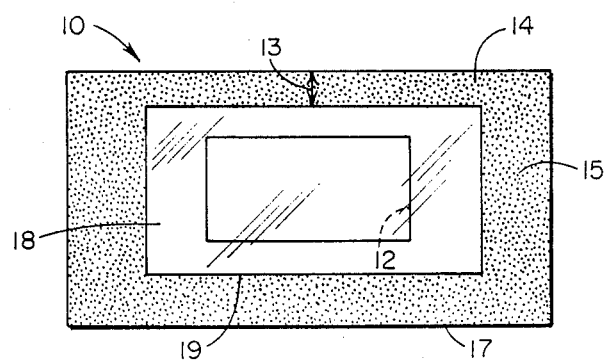
FIG. 3 is a bottom view of transparent bandage 10 of FIG. 1.

Referring now to the figures, wherein like parts are represented by like reference numerals, FIGS. 1-3 illustrate a first embodiment of the present invention designated by reference numeral 10. In the first embodiment, a transparent bandage 10 is shown that is particularly suitable for use in covering the wound of a medical patient. The transparent bandage 10 is designed such that it includes a centrally located opening 12. A frame surrounds the opening 12 such that a window is created at the center of the bandage 10.

The frame is preferably composed an stretchable adhesive electrode foam material. Suitable materials for the frame include the adhesive foam marketed under the federal trademark "MACROLYTE" by the Conmed Company or marketed under the trademarked name, "MICROFOAM" by the 3-M Company. The advantages of such material is that they are sufficiently flexible to be comfortably worn by the patient while being sufficiently rigid to retain the shape of the bandage when not adhered to the skin. Thus, the frame insures that the bandage will not fold upon itself during application or not retain its shape when packaged. Moreover, the foam material is substantially water-resistant, thus providing a barrier to contamination by bacteria or liquids.

While the shape of frame 14 is shown as being rectangular in FIGS. 1 through 3, it can be formed into any desired configuration. It is to be noted that by incorporating different shapes and sizes, the bandage can more effectively accommodate different parts of the body. Thus, different shapes would necessarily be contemplated by the present invention to cover elbows, knees, fingers, bony prominences or tubes or the like. For example, it is contemplated that the frame can be substantially oval, triangular or formed into a fanciful design such as a star, fish or heart. Other shapes of the present invention are illustrated in the remaining figures.

Returning now to FIG. 1, the opening 12 is enclosed along the bottom side by a transparent membrane 18. The membrane is adhered to frame 14 in such a manner that it cannot easily separate during use.

The material of the membrane 18 is preferably a hypo-allergenic non-adhesive flexible plastic that allows vapor and gasses to escape through the material in one direction but blocks contaminants and moisture from coming into the material in a second direction. It is preferred that the material for membrane 18 is "TEGADERM TM" marketed by the 3-M Company. However, any other material having similar characteristics as described above can be employed.

The frame 14 is coated on its bottom surface with a medical grade adhesive, preferably a hypo-allergenic synthetic acrylic pressure sensitive adhesive. The adhesive is used to secure the membrane 18 to the frame 14 as well as secure the frame 14, to the patient's skin. The acrylic adhesive is of sufficient tackiness to seal the wound from liquids or air seepage between the base of frame 14 and the patient's skin. The adhesive thus serves in combination with the frame as a water tight barrier between the interior of the bandage and the exterior environment. However, the adhesive is sufficiently weak that the bandage 10 can be removed with a minimum of resistance.

FIG. 2 shows a cut-away view of a cross-section of bandage 10 taken along reference lines II—II of FIG. 1. The membrane 18 is substantially smaller in width than the width of frame 14. When frame 14 is adhered to the membrane 18 by means of adhesive layer 15, those portions of frame 14 that extend beyond the membrane serve as an adhesive border that is used to adhere the bandage 10 to the patient's skin. Although adhesive layer 15 is shown as covering the entire bottom surface of frame 14, different types of adhesives can be used on different portions of frame 14. For example, a stronger adhesive can be employed to adhere the membrane 18 to the frame portion 14 while a weaker adhesive can be used along the adhesive border.

In a preferred embodiment, a liner 16 extends substantially across the adhesive border of frame 14 and the entire bottom surface of membrane 18. As shown, liner 16 adheres against the membrane by the tacky adhesive surface 15. By employing liner 16, the membrane 18 is protected and the tacky adhesive surface 15 remains unexposed during transport. In use, the liner 16 is peeled off of the frame 14 exposing the tacky adhesive surface for contact with a patient's skin. The materials of the liner can consist of any conventionally used paper or plastic liner.

FIG. 3 is a bottom view of the first embodiment illustrated in FIG. 1. More particularly, FIG. 3 shows the relationship between the membrane 18 and the frame 14. The perimeter 17 of the frame 14 is of such dimension that it is substantially wider and longer than the perimeter 19 of the membrane 18. As a result of this difference in perimeters, a border area defined by arrow 13 is formed around the membrane 18. As the adhesive material 15 covers the border 13 the border provides a complete adhesive frame around the non-adhesive bottom surface of the membrane 18. The wound area which is primarily covered by the membrane 18 will thereby not contact adhesive surface 15.

Figure 4:
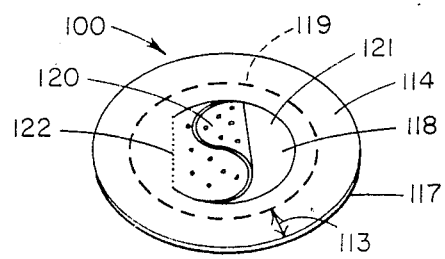
FIG. 4 is a perspective view of a second embodiment of a transparent bandage according to the present invention.

Referring now to FIG. 4, a second embodiment 100 consisting of a circular bandage is shown. The bandage according to the second preferred embodiment of the invention is generally similar in construction to the first embodiment described in conjunction with FIGS. 1-4. One major difference between the first and the second embodiments is flap 120 for covering the transparent opening 121 to be described below.

The bandage 100 includes a frame 114 composed of a medical grade foam that is similar to that described for use with the first preferred embodiment. The base 114 is coated with a medical grade adhesive (not shown) along its bottom surface in order to adhere a transparent membrane to the frame and the frame to the patient's skin. The adhesive, in turn, can secure a circularly shaped membrane material 11 such that it surrounds and covers the opening 121. The circumference 119 of the membrane 118 is less than the circumference of frame 114. Thus, a border referenced by radial arrow 113 is defined by the differences in size of these two elements. As previously discussed, the tacky adhesive surface (not shown) on the border of frame 14 is employed to adhere the circular bandage 100 to the skin.

The dressing further includes a flap 120 which is formed integrally with the frame 114. As shown, the flap is configured to substantially fit within opening 121 to cover the surface of transparent membrane 118. In order to open the flap, it is folded back towards the frame along fold line 122.

Although the flap 120 is shown to be configured to fit within opening 121, alternate shapes and constructions can be used. For example, flap 120 can be shaped to extend beyond the edge of opening 121 (not shown). The advantage of this latter design is that a person can readily grip the edge of flap 120 extending beyond the opening 121. The material of the flap can also be modified so as to allow air/vapor passage out to the exterior of the bandage. Such materials can include, but not be limited to an opaque "TEGADERM" sheet having the same characteristics as membrane 18. Alternatively, the flap can be made of the same material as that of the frame 114 but can further include a plurality of air holes to allow air passage into and out of opening 121.

FIGS. 5a, 5b and 6 each illustrate trachea tube holder embodiments 200 and 250 yielding many of the aforedescribed advantages of the first two embodiments described above in FIGS. 1-4.

The trachea tube holder 200 shown in FIG. 5a includes a frame 214 formed of similar material to that described with reference to the first and second embodiments. The frame substantially surrounds an opening 221. As previously described, the opening is then covered by a transparent membrane portion 218 formed of a similar transparent material described above. Located at the center of the membrane 218 is a tube hole 225 and a tube hole collar 229. The material of collar 229 can be the same stretchable, medical foam used with regard to frame 214 although the collar 229 is located both above and below membrane 218. In addition, an adhesive layer is coated on the upper collar 229 and the collar below membrane 218 in order that the collar adheres both to the skin around the trachea tube and to the cuff of the tube itself. A slit 227 extends through frame 214, membrane 218, collar 229 to tube hole 225 to enable the trachea tube holder 200 to sufficiently open up to accommodate insertion of the tube into hole 225 and inside the collar 229. In addition to trachea tubes, the bandage of FIG. 5a is adaptable for use as a stoma or fisula dressing.

FIG. 5b illustrates a fourth embodiment of the present invention. As shown, an oval trachea tube holder 250 includes a foam frame 264 formed of a similar material to that described above. The frame defines an opening 221 which is substantially covered by a vapor and gas permeable transparent membrane 268. An upper collar 279 made of a tacky foam material, in turn, surrounds a tube hole 275 centrally located in membrane 268. Moreover, a slit 277 is formed extending radially from tube hole 275 to the edge of frame 264.

FIG. 6 illustrates the fifth embodiment 200 for use on the neck of patient 280. The trachea tube holder 200 is adhered to a user's skin by the adhesive layer on frame 214. A tracheal tube 282 is secured at its cuff (not shown) by collar 229. A slit 227 opens the bandage 200 to accommodate the curve of the patient's neck. The tube is held firmly to the bandage 200 by means of adhesive collar 229 such that the skin around the trachea tube is both visible and substantially covered by membrane 218.

FIG. 7 illustrates a sixth embodiment 300 of the transparent bandage suitable for special application over raised portions of a patient's body. The frame 314 is formed of a substantially similar stretchable foam material to that described above. However, the frame includes a pair of finger portions 330 located at opposed ends such that the overall "H" shaped frame is formed. The arrangement of membrane 318, opening 312 and adhesive border 320 are identical to that described in the first through fourth embodiments of the present invention.

FIG. 8 illustrates a seventh embodiment of the present invention 400. As shown, the construction of bandage 400 is identical to the first embodiment (FIG. 1) except for slit 410 along one side of frame 408. The bandage of FIG. 8 is useful for securing any tube or line that must enter a sterile field under the membrane 418. The bandage 400 is of particular importance for Hickman catheters, jugular intra-venous lines, central intra-venous catheter dressings and gastrostomy tube dressings.

The slit 410 is incorporated into the frame 408 in order to prevent contaminants from entering the wound site. This is accomplished by using the slit 410 as the channel through which a tube 69 is inserted into the bandage as shown in FIG. 9b. When the tube 69 is placed in the slit, the slit closes along the sides of the tube, sealing the area around the tube 69 from contaminant/moisture seepage into the puncture site. Thus, the use of the slit avoids the drawback of having the bandage 10 lift up as shown in FIG. 9a around the edges of the tube 69. By keeping the wound site sterile, the infection potential about the wound is substantially decreased.

The bandages shown in the various embodiments of the present invention also have the advantages of maintaining an effective barrier to allow for the insertion of various medications and salves, without spillage. Such materials can be contained close to the wound while the bandage and its foam frame enables a patient to shower or even submerge the dressing without affecting such medications.

The bandage as described in the preferred embodiments is shown in use in a hospital setting. Although, as already pointed out, the bandage may be used in other settings both medical, and non-medical for holding articles to objects or for securing and sealing objects. For example, one such contemplated setting is in the electronics industry where transparent sealing devices may be used to secure wires within, around or between equipment. Another application is in shipping for holding labels to boxes, in dentistry for securing tubes to a patient's mouth or in packaging for containing spoilable goods in a breathable package.

What is new and desired to be protected by Letters Patent of the U.S. is:

1. A dressing for covering a patient's skin comprising:
an outer skin-contacting layer having an opening substantially surrounded by said outer layer
a pliable transparent inner skin-contacting membrane positioned throughout said opening wherein a perimeter of said outer layer substantially surrounds said membrane; and
an adhesive layer on a bottom surface of said outer layer such that said membrane is secured to a portion of said outer layer and said perimeter of said outer layer forms an adhesive perimeter in order that said dressing is adhered to such patient's skin only at said adhesive perimeter.

2. The dressing according to claim 1, wherein said outer layer is formed of a semi-rigid foam material.

3. The dressing according to claim 2, wherein said transparent membrane consists of an air permeable pliable material such that said dressing allows visual observation of such patient's skin.

4. The dressing according to claim 2, further comprising a liner located below said membrane and attached to said adhesive perimeter, exposing said adhesive perimeter for contact with such patient's skin.

5. The dressing according to claim 4, wherein said liner consists of a paper material.

6. The dressing according to claim 1, wherein said outer layer, said membrane and said opening are rectangular.

7. The dressing according to claim 1, wherein said outer layer, said membrane and said opening are circular.

8. The dressing according to claim 1, wherein said outer layer further comprises a pair of finger portions, each pair extending from opposed ends of said outer layer such that said outer layer forms a substantially "H" shaped dressing.

9. A dressing for a patient's skin, comprising:
an outer layer surrounding a window opening;
a pliable transparent inner skin-contacting layer attached to said outer layer and extending throughout said window opening; and
an adhesive border formed on said outer layer around the perimeter of said inner layer such that when adhered to such patient's skin a chosen area of skin shows through said window opening.

10. A method for applying a dressing comprising a pliable transparent membrane attached at its perimeter to a semi-rigid adhesive border having a liner secured to said adhesive border, comprising the steps of:
removing said liner from said adhesive border in order to expose a tacky adhesive surface;
centering said transparent membrane over a wound such that said window contacts such wound; and
applying said dressing to such wound in order that said tacky adhesive surface substantially contacts skin surrounding such wound rendering such wound entirely visible through said transparent membrane as well as isolated from contact with said semi-rigid adhesive border.

11. A dressing for covering a patient's skin, comprising:
an adhesive frame having an opening substantially surrounded by said adhesive frame; and
a pliable transparent non-adhesive skin-contacting membrane attached to said frame and extending throughout said opening where a portion of said adhesive frame extends beyond said membrane and forms an adhesive border to substantially adhere said transparent dressing to such skin at said adhesive border.

12. The dressing according to claim 11, wherein said adhesive frame is formed of a semi-rigid foam material.

13. The dressing according to claim 11, wherein said adhesive frame consists of a single piece of material.

14. The dressing according to claim 11, wherein said adhesive frame substantially retains the shape of said dressing when packaged.

15. The dressing according to claim 11, wherein said transparent membrane consists of an air permeable pliable material such that said dressing allows visual observation of a patient's wound.

16. The dressing according to claim 11, wherein said transparent membrane is hypo-allergenic allowing the passage of vapor and gases through said transparent membrane in one direction and blocking contaminants and moisture coming into said transparent membrane in a second direction.

17. The dressing according to claim 11, further comprising a liner located on a skin contacting surface of said transparent membrane and attached to said adhesive border such that said liner is adapted to be peeled off of said adhesive border, exposing said adhesive border and transparent membrane to a patient's skin.

18. The dressing according to claim 17, wherein said liner consists of a paper material.

19. The dressing according to claim 11, wherein said adhesive frame is coated with a hypo-allergenic synthetic acrylic pressure sensitive adhesive of sufficient tackiness to seal a wound from a liquid and/or air seepage into said dressing.

20. The dressing according to claim 19, wherein a first adhesive is employed to adhere said transparent membrane to said adhesive frame and a second adhesive is employed to adhere to said transparent dressing to such patient's skin.

21. A transparent dressing for covering a patient's wound, comprising:

a frame having an opening substantially surrounded by said frame;
a transparent non-adhesive skin-contacting membrane positioned below said frame and throughout said opening wherein a perimeter of said frame substantially surrounds said transparent membrane;
an adhesive layer on a skin contacting surface of said frame such that said membrane is secured to a portion of said frame and said frame portion that extends beyond said membrane forms an adhesive border enabling said transparent dressing to be adhered to a patient's skin at said adhesive border; and
a flap for substantially covering said opening.

22. The dressing according to claim 21, wherein said flap is formed integrally with said frame.

23. The dressing according to claim 21, wherein said flap is made of a substantially air permeable material.

24. The dressing according to claim 21, wherein said flap has a plurality of air holes such that gas passes through said flap.

25. The dressing according to claim 21, wherein the perimeter of said flap is larger than the perimeter of said opening.

* * * * *